US009835581B2

(12) United States Patent
Chapples et al.

(10) Patent No.: US 9,835,581 B2
(45) Date of Patent: Dec. 5, 2017

(54) GAS SENSOR USING AN IONIC LIQUID ELECTROLYTE

(71) Applicant: Honeywell International Inc., Morristown, NJ (US)

(72) Inventors: John Chapples, Portsmouth (GB); Martin Geoffrey Jones, Havant (GB)

(73) Assignee: Honeywell International, Inc., Morris Plains, NJ (US)

( * ) Notice: Subject to any disclaimer, the term of this patent is extended or adjusted under 35 U.S.C. 154(b) by 684 days.

(21) Appl. No.: 14/037,959

(22) Filed: Sep. 26, 2013

(65) Prior Publication Data
US 2015/0083592 A1 Mar. 26, 2015

(51) Int. Cl.
*G01N 27/403* (2006.01)
*G01N 27/404* (2006.01)
*G01N 33/00* (2006.01)
*G01N 27/30* (2006.01)

(52) U.S. Cl.
CPC ....... *G01N 27/4045* (2013.01); *G01N 27/308* (2013.01); *G01N 33/0044* (2013.01)

(58) Field of Classification Search
CPC ............ G01N 27/404–27/4045; G01N 27/413
See application file for complete search history.

(56) References Cited

U.S. PATENT DOCUMENTS

| | | | | |
|---|---|---|---|---|
| 5,173,166 A * | 12/1992 | Tomantschger | ... | G01N 27/4045 204/412 |
| 2010/0236924 A1 * | 9/2010 | Chapples | ............. | G01N 27/404 204/412 |
| 2011/0226619 A1 * | 9/2011 | Eckhardt | .............. | G01N 27/401 204/417 |
| 2011/0284386 A1 * | 11/2011 | Willey | ..................... | C25D 3/38 205/96 |
| 2013/0087456 A1 * | 4/2013 | Pratt | .................. | G01N 27/4163 204/406 |

FOREIGN PATENT DOCUMENTS

| | | |
|---|---|---|
| AU | 2014227438 B2 | 4/2016 |
| CA | 2864320 A1 | 3/2015 |
| CN | 104515795 A | 4/2015 |
| DE | 10 2008 044238 A1 | 6/2010 |
| EP | 1 544 614 A1 | 6/2005 |
| EP | 2 226 627 A1 | 9/2010 |
| EP | 2853890 A1 | 4/2015 |

(Continued)

OTHER PUBLICATIONS

Extended search report and examination for corresponding EP patent application 14184169.2, dated Dec. 5, 2014.

(Continued)

*Primary Examiner* — Gurpreet Kaur
(74) *Attorney, Agent, or Firm* — Conley Rose, P.C.

(57) ABSTRACT

A gas sensor having a housing with first and second chambers featuring a porous separator located there between. The first chamber of the sensor being connected to atmosphere via a gas diffusion aperture. The gas sensor having a sensing electrode disposed within the first chamber and at least a second electrode disposed within the second chamber. The sensor having an ionic liquid electrolyte disposed within the second chamber where the sensing electrode and at least second electrodes comprise platinum.

17 Claims, 6 Drawing Sheets

Comparison of the Cross-Sensitivities to Various Gases of Sensors with Platinum Sensing Electrodes & Different Electrolytes

| Test Gas | | Electrolyte System | | | | | |
|---|---|---|---|---|---|---|---|
| Type | Concentration | Mean Gas Sensitivity (nA/ppm) | | | Mean Normalised Gas Sensitivity (% wrt $H_2S$) | | |
| | ppm | 5M $H_2SO_4$ | EMIMHS + MSA | DMEATFSI + HTFSI | 5M $H_2SO_4$ | EMIMHS + MSA | DMEATFSI + HTFSI |
| Hydrogen Sulphide | 19 | 4339 | 3003 | 927 | 100 | 100 | 100 |
| Carbon Monoxide | 204 | 281 | 6 | 10 | 6 | 0 | 1 |
| Hydrogen | 200 | 4 | 25 | 8 | 0 | 1 | 1 |
| Nitrogen Dioxide | 19 | -904 | -797 | -92 | -21 | -27 | -10 |
| Nitric Oxide | 49 | -7 | -14 | 55 | 0 | 0 | 6 |
| Sulphur Dioxide | 203 | 800 | 638 | 116 | 18 | 21 | 12 |
| Hydrogen Chloride | 150 | 45 | 25 | 45 | 1 | 1 | 5 |
| Ammonia | 53 | 0 | 3 | 83 | 0 | 0 | 9 |
| Ethylene | 200 | 42 | 1 | 13 | 1 | 0 | 1 |
| Ethanol | 196 | 142 | 1 | 136 | 3 | 0 | 15 |

Notes: EMIMHS = 1-Ethyl-3-methylimidazolium hydrogensulfate (hydrophilic ionic liquid)
DMEATFSI = N,N-Dimethylethanolammonium bis(trifluoromethylsulfonyl)amide (hydrophobic ionic liquid)
MSA = Methanesulfonic acid (doping conc = 0.1 mol/kg)
HTFSI = Bis(trifluoromethane)sulfonimide (doping conc = 0.1 mol/kg)
Sensing & counter electrodes both platinum black

(56) References Cited

FOREIGN PATENT DOCUMENTS

| JP | 2006-98269 | 4/2006 |
|---|---|---|
| WO | WO 2010/063624 A1 | 6/2010 |
| WO | WO 2011/151637 A1 | 12/2011 |
| WO | 2012071151 A1 | 5/2012 |
| WO | WO 2013/052041 A1 | 4/2013 |

OTHER PUBLICATIONS

Wei et al., Applications of ionic liquids in electromechanical sensors, Analytica Chimica Acta, Dec. 23, 2007, pp. 126-135, vol. 607, No. 2, Elsevier, Amsterdam NL.
O'Mahony et al., The Mediated Detection of Hydrogen Sulfide in Room Temperature Ionic Liquids, Electroanalysis, Aug. 3, 2010, pp. 2313-2322, vol. 22, No. 20.
Canada Patent Application No. 2,864,320, Examination Report, dated Dec. 9, 2015, 5 pages.
Canada Patent Application No. 2,864,320, Examination Report, dated Nov. 9, 2016, 4 pages.
Australia Patent Application No. 2014227438, Patent Examination Report No. 1, dated Jun. 3, 2015, 3 pages.
Australia Patent Application No. 2014227438, Notice of Acceptance, dated Dec. 16, 2015, 2 pages.
Australia Patent Application No. 2016202181, Patent Examination Report No. 1, dated May 3, 2017, 5 pages.

* cited by examiner

Figure 1  2-Electrode Sensor Assembly used for Evaluating Ionic Liquid Electrolytes
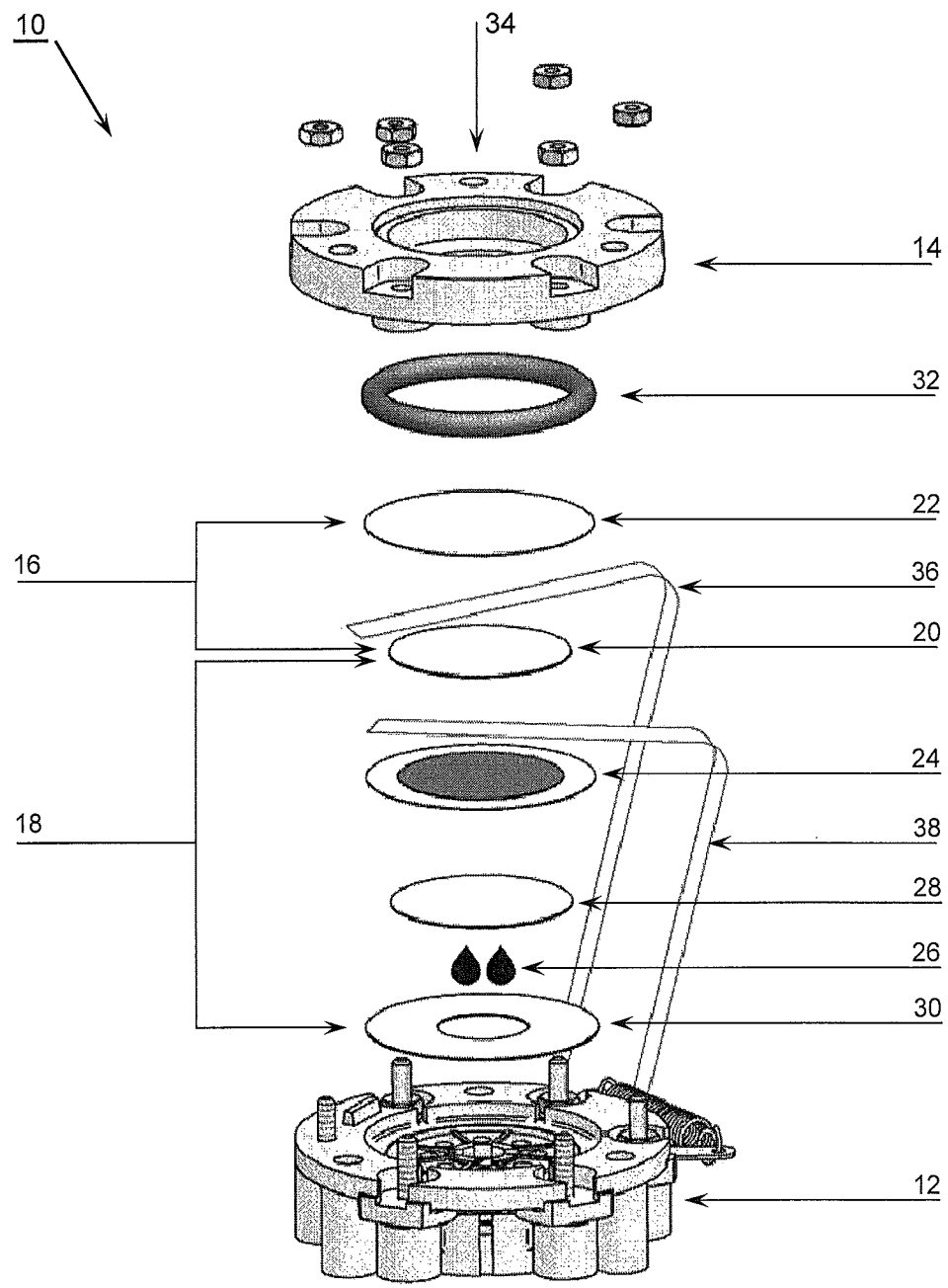

Figure 2  Comparison of the Cross-Sensitivities to Various Gases of Sensors with Platinum Sensing Electrodes & Different Electrolytes

| Test Gas | | Electrolyte System | | | | | |
|---|---|---|---|---|---|---|---|
| Type | Concentration | Mean Gas Sensitivity (nA/ppm) | | | Mean Normalised Gas Sensitivity (% wrt $H_2S$) | | |
| | ppm | 5M $H_2SO_4$ | EMIMHS + MSA | DMEATFSI + HTFSI | 5M $H_2SO_4$ | EMIMHS + MSA | DMEATFSI + HTFSI |
| Hydrogen Sulphide | 19 | 4339 | 3003 | 927 | 100 | 100 | 100 |
| Carbon Monoxide | 204 | 281 | 6 | 10 | 6 | 0 | 1 |
| Hydrogen | 200 | 4 | 25 | 8 | 0 | 1 | 1 |
| Nitrogen Dioxide | 19 | -904 | -797 | -92 | -21 | -27 | -10 |
| Nitric Oxide | 49 | -7 | -14 | 55 | 0 | 0 | 6 |
| Sulphur Dioxide | 203 | 800 | 638 | 116 | 18 | 21 | 12 |
| Hydrogen Chloride | 150 | 45 | 25 | 45 | 1 | 1 | 5 |
| Ammonia | 53 | 0 | 3 | 83 | 0 | 0 | 9 |
| Ethylene | 200 | 42 | 1 | 13 | 1 | 0 | 1 |
| Ethanol | 198 | 142 | 1 | 138 | 3 | 0 | 15 |

Notes: EMIMHS = 1-Ethyl-3-methylimidazolium hydrogensulfate (hydrophilic ionic liquid)
DMEATFSI = N,N-Dimethylethanolammonium bis(trifluoromethylsulfonyl)amide (hydrophobic ionic liquid)
MSA = Methanesulfonic acid (doping conc = 0.1 mol/kg)
HTFSI = Bis(trifluoromethane)sulfonimide (doping conc = 0.1 mol/kg)
Sensing & counter electrodes both platinum black

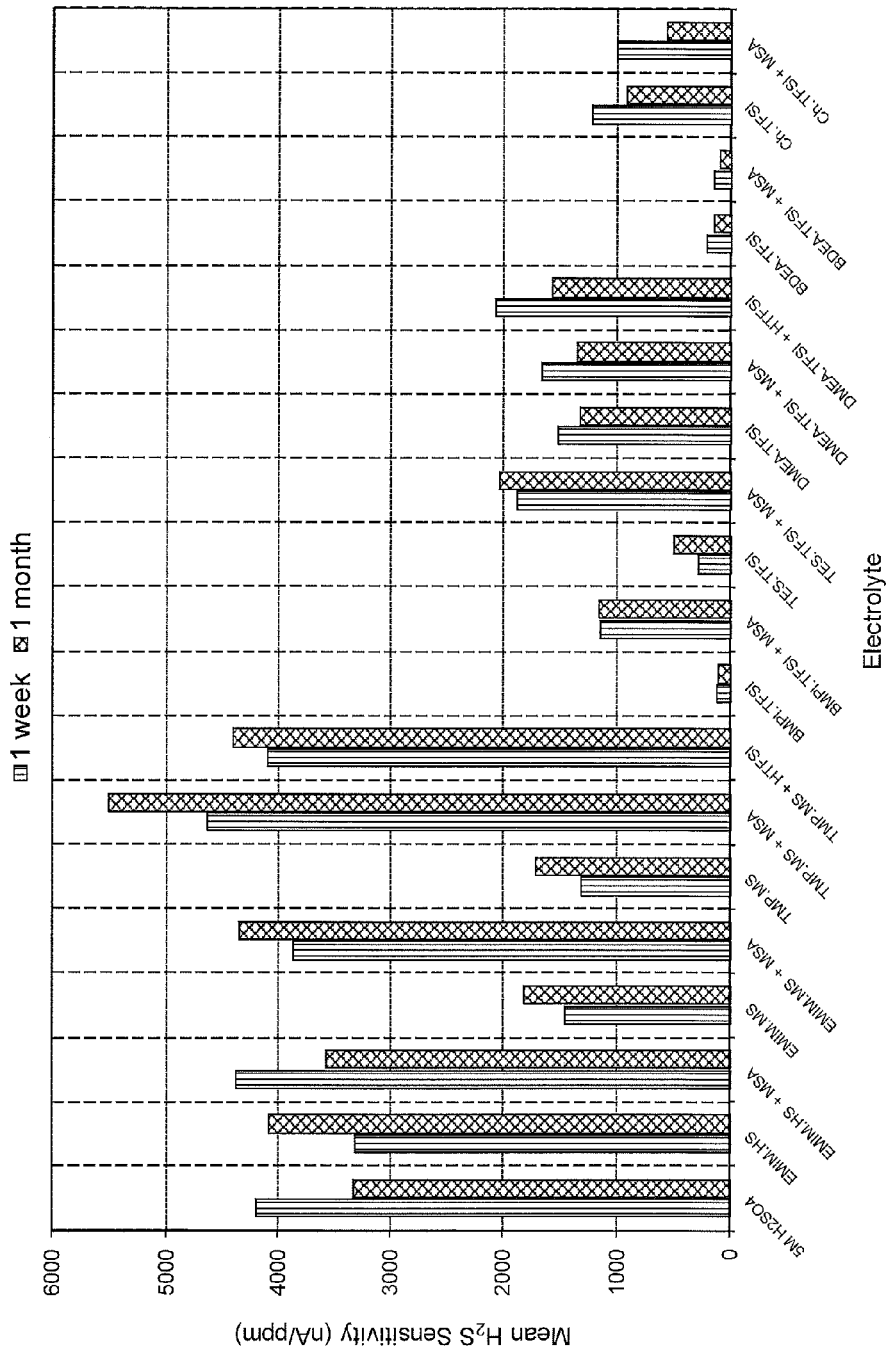
Figure 3 Comparison of the Hydrogen Sulfide Sensitivities shown by Sensors using Different Pure and Acid Doped Ionic Liquids as Electrolytes

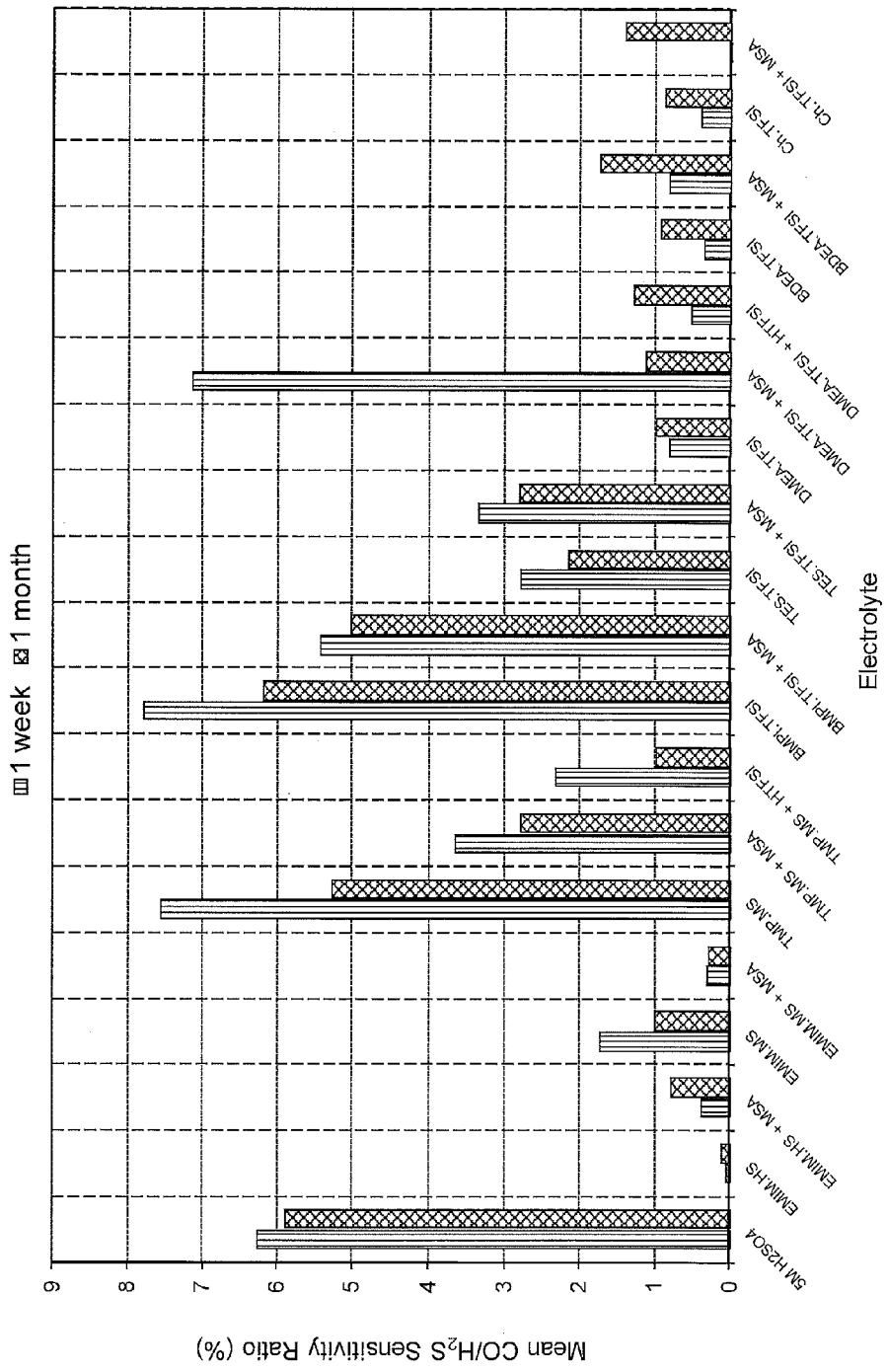
Figure 4 Comparison of the Carbon Monoxide Cross-Interferences shown by Sensors using Different Pure and Acid Doped Ionic Liquids as Electrolytes

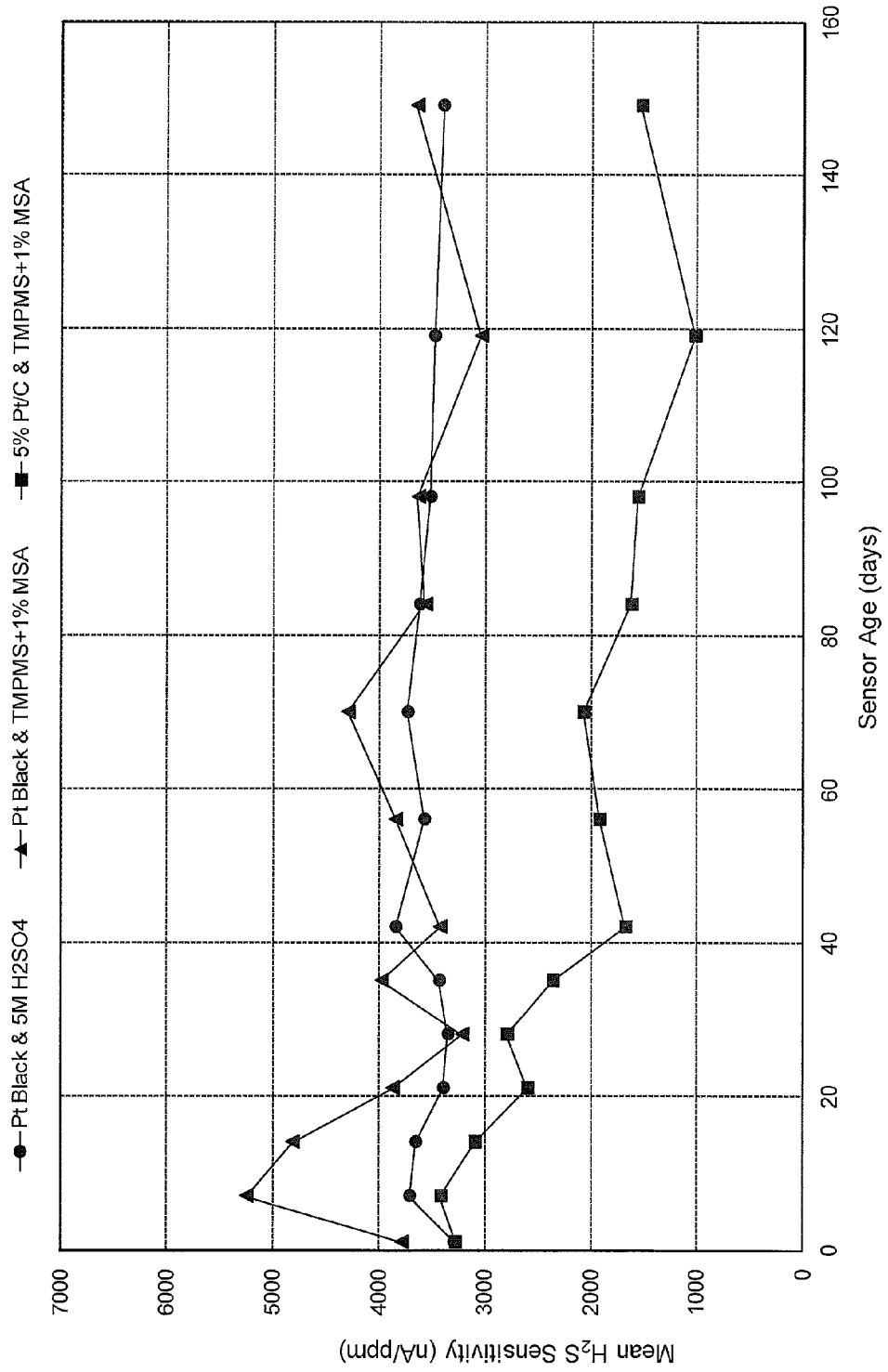
Figure 5  Comparison of the Effect of Aging on the Hydrogen Sulfide Responses of Sensors built with different Electrolytes and Sensing Electrode Catalysts

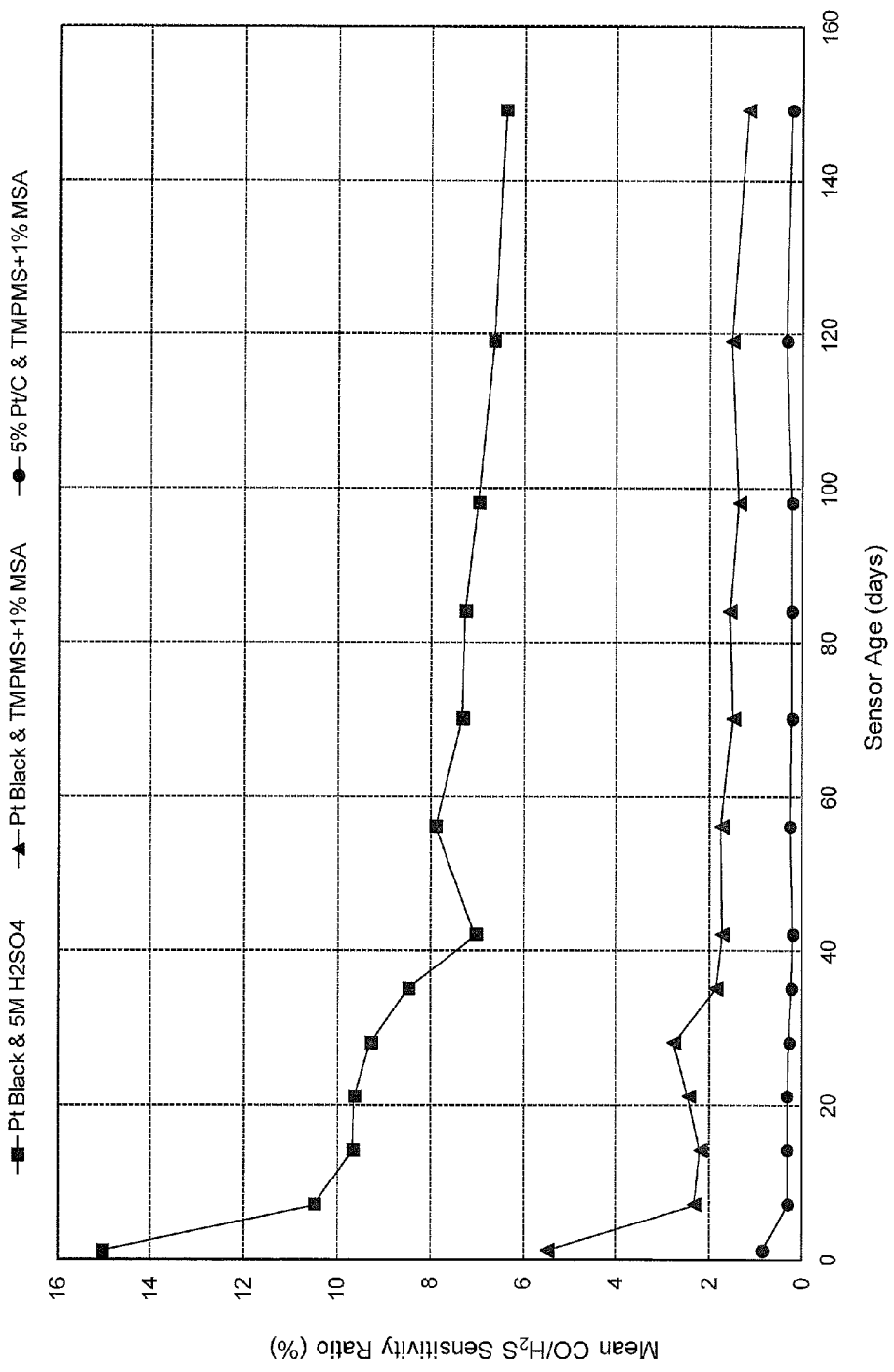
Figure 6  Comparison of the Effect of Aging on the Carbon Monoxide Cross-Interferences of Sensors built with different Electrolytes and Sensing Electrode Catalysts

GAS SENSOR USING AN IONIC LIQUID ELECTROLYTE

FIELD

The field relates to gas sensors and more particularly to gas sensors using ionic liquids as electrolytes.

BACKGROUND

Electrochemical gas sensors traditionally comprise a gas diffusion working or sensing electrode, often based on a metal catalyst dispersed on PTFE tape. A target gas reacts at this electrode while a balancing reaction takes place at the counter electrode, which may also be a gas diffusion electrode. The electrodes are held within an outer housing which usually contains a liquid electrolyte capable of supporting the relevant reactions (e.g., sulfuric acid). The gas under test typically enters the housing through a controlled diffusion access port which regulates the ingress of the target gas into the cell. As the target gas is reacted at the sensing electrode, the electrical output of the sensor may be directly related to the ambient target gas concentration. Such principles are well known and have been described.

There are a number of key performance parameters which limit the use of electrochemical gas sensors in aggressive environments. One of these is the ability of the sensor to function for extended periods in extremes of temperature and/or humidity. Traditional electrolytes are often based on aqueous systems which have particular weakness in this regard. Clearly it is desirable for the sensor's working lifetime to be as long as possible but moreover it is important that any particular sensor type will consistently continue to work for at least the indicated lifetime. Early failures lead to the need for more frequent sensor replacement, as well as increased checking and monitoring of sensor performance and, ultimately, a loss in confidence in the sensor. Accordingly, there is a need to produce sensors that are more stable under many different operating environments. There has been some progress in improving this behavior by using novel electrolyte systems such as those based on ionic liquids.

A further limitation of some current electrochemical gas sensors is that the available electrode options do not have the required level of specificity toward the target gas. This can require the use of filters to improve the selectivity, which can in turn introduce further operational difficulties.

Some electrode types are also relatively expensive to manufacture, usually due to the presence of comparatively high loadings of precious metal catalysts. Unfortunately, many conventional supported catalysts (which could be used as a cheaper alternative) are not stable in the aggressive electrolytes currently employed, which further limits the available options.

We have demonstrated that the behavior of electrode-electrolyte systems is affected in previously unanticipated ways by switching from conventional (aqueous) electrolytes to those based on ionic liquids. This has been shown to offer the sensor designer a range of alternative tools and options which can solve key operational problems.

In particular, we have shown that the same electrode material (e.g. Pt) used to detect a particular target gas (e.g. $H_2S$) will demonstrate quite different relative sensitivities towards potential gas phase interferents, depending on the electrolyte system used. We have identified key differences in behavior between conventional and ionic liquid electrolytes, as well as between different types of ionic liquid electrolyte. This effect can have a major impact in practical applications, where conventional electrolytes may require other means (e.g. filters) to ensure that a reliably specific measurement of the target gas is obtained.

We have also noted that some electrode choices which might otherwise be commercially preferred are currently excluded by cross interference effects. Thus for $H_2S$ sensors using conventional $H_2SO_4$ based electrolyte, pure Pt is not a viable choice due to the magnitude of its CO cross interference. The usual solution is to employ Ru/Pt or Ir. However, these are more susceptible to poisoning, generally offer lower activity and are less amenable to conventional electrode manufacturing processes. Pt/carbon mixtures, which might offer a means to reduce the unwanted CO interference, cannot be employed because the carbon is prone to slow oxidation at anodic potentials in acid electrolyte media, giving rise to long term instability. However, this problem can be eliminated by the appropriate choice of ionic liquid electrolyte, where the different cross sensitivity behavior offered provides new options to the sensor designer. This approach enables resolution of some key practical operating problems.

A further example relates to oxygen pump sensors where oxygen is reduced at the working electrode and evolved at the counter. This system normally employs acidic electrolytes similar to those used in many toxic gas sensors and so the use of carbon-supported Pt catalysts for oxygen reduction is again unfavorable due to their poor stability in this environment. However, major cost savings can be obtained by the reduction of precious metal loading facilitated by the use of carbon-supported catalysts. This can in principle be facilitated by the use of an ionic liquid electrolyte, in which the carbon is much more stable.

BRIEF DESCRIPTION OF THE DRAWINGS

FIG. 1 is an exploded view of the sensor used as a test vehicle for evaluating various ionic liquids as electrolytes;

FIG. 2 illustrates performance data for sensors of the type shown in FIG. 1 built with several electrolytes and exposed to a number of different interferent gases of interest;

FIG. 3 illustrates performance data for sensors of the type shown in FIG. 1 built with a wider variety of electrolytes and exposed to the key target gas $H_2S$;

FIG. 4 illustrates cross-interference data presented as a percentage of the primary $H_2S$ signal for sensors of the type shown in FIG. 1 built with the same electrolytes presented in FIG. 3;

FIG. 5 shows the performance of sensors of FIG. 1 using the ionic liquid 1,2,4-trimethylpyrazolium methylsulfate doped with 1% methanesulfonic acid as electrolyte in combination with platinum black or 5% platinum on carbon sensing electrodes and sensors of FIG. 1 using conventional sulfuric acid electrolyte with platinum black sensing electrodes in response to hydrogen sulfide as a function of age;

FIG. 6 shows the performance of sensors of FIG. 1 using the ionic liquid 1,2,4-trimethylpyrazolium methylsulfate doped with 1% methanesulfonic acid as electrolyte in combination with platinum black or 5% platinum on carbon sensing electrodes and sensors of FIG. 1 using conventional sulfuric acid electrolyte with platinum black sensing electrodes for cross-interference response to carbon monoxide as a function of age.

DETAILED DESCRIPTION OF AN ILLUSTRATED EMBODIMENT

FIG. 1 depicts an electrochemical gas sensor 10 shown generally in accordance with an illustrated embodiment. The gas sensor 10 is incorporated into a housing including a body 12 and top cover 14 that may be sealed together via an O-ring 32 and a floor seal 30.

The body 12 and cover 14 define an internal space. The internal space is effectively divided into a first chamber 16 and second chamber 18 by a separator 20.

Located in the first chamber 16 is a sensing electrode 22. At least a second electrode 24 is located in the second chamber 18. The sensing and second electrodes 22, 24 are electrically coupled to a connector located on the outside of the body 12 via respective conductors 36, 38.

An aperture 34 extends through the cover 14. The aperture 34 allows a target gas to enter the first chamber 16 and interact with the sensing electrode 22.

The second chamber 18 is filled with an electrolyte 26. The electrolyte 26 saturates the separator 20 thereby causing the separator 20 to form an ionic connection between the sensing and second electrodes 22, 24. Another porous member 28 in the second chamber 18 acts as a reservoir of electrolyte 26 that helps to keep the separator 20 between the electrodes 22, 24 saturated with electrolyte 26.

The sensor 10 may be used to sense a number of different target gases. In one preferred embodiment, the sensor 10 may be used to sense hydrogen sulfide.

In this regard, amperometric electrochemical hydrogen sulfide sensors typically use ruthenium/platinum or iridium sensing electrodes with a sulfuric acid electrolyte in either a two-electrode or zero-biased three electrode configuration. Pure platinum could not be used in the past because it was found that platinum used with sulfuric acid has an unacceptably high cross sensitivity to carbon monoxide, a common interfering gas in the intended applications.

However, platinum electrodes, especially in the form of carbon-supported platinum are cheaper and easier to manufacture than ruthenium/platinum or iridium electrodes, but cannot be used with a sulfuric acid electrolyte. When used in such environments, carbon is thermodynamically unstable at platinum rest potentials in sulfuric acid and will be oxidized, thereby resulting in the degradation and possibly even the eventual failure of the electrode.

In addition, platinum is less susceptible to poisoning by other gases than ruthenium based alloys and is more active and is more commercially available. In addition, platinum electrodes are often provided in the form of platinum decorated electrodes which are effectively microdot arrays and therefore have more effective mass transport towards the catalyst.

In one illustrated embodiment, the sensor 10 makes use of an electrolyte that allows platinum to be used without giving a significant CO response. Additionally, the use of a non-oxidizing electrolyte allows platinum/carbon electrodes to be used, again, without giving a significant CO response.

Currently available electrochemical gas sensors using conventional aqueous based acid electrolytes such as sulfuric acid are commonly prone to cross-interferences from gases other than the primary target gas. Consequently, this behavior has the potentially deleterious effect of producing a sensor response that can subsequently give rise to false instrument hazard alarms. Some methods of improving the gas selectivity of electrochemical sensors already exist, such as modifying operating bias potential, introducing chemical filters, and choice of the sensing electrode catalyst. However these are often limited in scope and do not always provide an effective means of reducing significant cross-interferences.

Under another embodiment, the sensor utilizes an ionic liquid based electrolyte that improves sensor selectivity towards the target gas hydrogen sulfide whilst reducing interference from other gas or vapor species. It also allows highly reactive electrode catalysts such as platinum to be used without the adverse effects of large cross-interferences normally associated with such materials when exposed to other reactive gas species. In some embodiments, the ionic liquid electrolyte is pure or acid doped and further comprises one of: 1-ethyl-3-methylimidazolium hydrogensulfate (EMIM.HS), EMIM.HS+methanesulfonic acid (MSA), EMIM.MS, 1-ethyl-3-methylimidazolium methylsulfate (EMIM.MS)+1,2,4-trimethylpyrazolium methylsulfate (TMP.MS), TMP.MS+MSA, TMP.MS+bis(trifluoromethane)sulfonimide (HTFSI), N-n-butyl-N-methylpiperidinium bis(trifluoromethane)sulfonimide (BMPL.TFSI), BMPL.TFSI+MSA, N,N,N',N'-tetraethylsulfamide (TES.TFSI), TES.TFSI+MSA, N,N-dimethylethanolamine bis(trifluoromethane)sulfonimide (DMEA.TFSI), DMEA.TFSI+MSA, DMEA.TFSI+HTFSI, butyldiethanolamine bis(trifluoromethylsulfonyl)imide (BDEA.TFSI), or BDEA.TFSI+MSA.

As an example of the art, conventional City Technology 3-series sensors in 2-electrode format were used for the evaluation tests. These were built with standard platinum black gas diffusion electrodes and filled with electrolytes consisting of either 1-ethyl-3-methylimidazolium hydrogensulfate or N,N-Dimethylethanolammonium bis(trifluoromethylsulfonyl)amide ionic liquids doped with 0.1 kg/mol methanesulfonic acid. Tests were subsequently conducted to assess their responses towards various gases and vapors which were cross-referenced to the typical outputs obtained in hydrogen sulfide. All the sensors were operated throughout at the platinum/air rest potential (i.e. no additional bias voltage was applied to the sensing electrode). The results are shown in FIG. 2, which demonstrates, for example, that the relative sensitivities of platinum electrodes toward CO, $NO_2$, NO, $NH_3$ and ethanol are affected by the choice of electrolyte employed.

FIG. 3 shows data for the particular example of the $H_2S$ responses of sensors. For Pt electrodes specifically, the behavior toward each gas is shown for a much wider range of both pure and acid doped ionic liquid electrolyte systems. FIG. 4 shows data for the corresponding CO interference signals of the sensors presented in FIG. 3 (which is a key issue in the field). It is clear that in principle, the interference can be reduced by an order of magnitude or more whilst retaining similar absolute $H_2S$ output levels by judicious choice of electrolyte system, i.e. the selection of ionic liquid and use of an acid dopant if appropriate.

Room temperature aprotic ionic liquids such as those listed in the attached FIGS. 2-3 are used as electrolytes 26 in sensors of the type shown in FIG. 1.

The attached FIGS. 5-6 compare the longer term performance of sensors using either Pt black or 5% Pt supported on carbon sensing electrodes in combination with the ionic liquid electrolyte 1,2,4-trimethylpyrazolium methylsulfate doped with 1% methanesulfonic acid toward $H_2S$ and CO. The pure Pt electrode is the conventional sensing electrode widely used in existing commercial toxic gas sensors. The same figures also compare the behaviour of the Pt black electrodes in combination with the conventional sulfuric acid electrolyte. It is clear that in the TMPMS+1% MSA example electrolyte system, Pt/graphite electrodes offers acceptable $H_2S$ sensitivity (closely comparable with that from the $Pt/H_2SO_4$ system), but with much lower CO cross interference. In addition, although FIGS. 5 and 6 illustrate the performance of sensors using 5% platinum on carbon sensing electrodes, it will be recognized that the 5% loading level is illustrated for exemplary purposes and higher or lower platinum loading levels can also be used without departing from the novel scope of the subject invention.

Generally, the approaches to structuring the sensor 10 may include the following considerations: First, liquids and other novel electrolytes have commonly been appraised in the previous art with the intention of improving the environmental operating range of gas sensors. Devices using conventional electrolytes such as sulfuric acid & other traditional aqueous electrolytes operate well in many circumstances but are limited primarily by water management issues when subjected to harsher environmental extremes. Overcoming these limitations has therefore been the main driver for their replacement and much existing IP in the past. However, current work has shown that other valuable performance attributes can be offered by ionic liquid electrolytes in addition to the usual environmental performance improvements. In particular, improved gas specificity can be achieved by selection of the appropriate ionic liquid electrolyte/electrode catalyst combination. Furthermore, the use of alternative electrode catalysts (particularly supported versions) which cannot be used in conjunction with the more aggressive traditional acid electrolyte systems becomes possible. These are the beneficial features that may be emphasized in particular within this description.

What is claimed is:

1. An apparatus comprising:
    a housing having first and second chambers with a porous separator located there between and with the first chamber connected to atmosphere via a gas diffusion aperture;
    a sensing electrode disposed within the first chamber;
    at least one additional electrode disposed within the second chamber;
    an acid doped ionic liquid electrolyte disposed within the second chamber, wherein the acid doped ionic liquid electrolyte comprises an ionic liquid electrolyte and an acid dopant, wherein the sensing electrode and the at least one additional electrode further comprise platinum, and wherein the ionic liquid electrolyte comprises 1,2,4-trimethylpyrazolium methylsulfate.

2. The apparatus as in claim 1, wherein at least one of the sensing electrode or the at least one additional electrode comprises platinum black.

3. The apparatus as in claim 1, wherein the apparatus comprises a hydrogen sulfide sensor with substantially no cross-sensitivity to carbon monoxide.

4. The apparatus as in claim 1, wherein at least one of the sensing electrode or the at least one additional electrode comprises substantially 5% platinum on the carbon.

5. The apparatus as in claim 1, wherein the acid doped ionic liquid electrolyte comprises about 1% acid doping.

6. The apparatus as in claim 1, wherein the acid doped ionic liquid electrolyte comprises about 0.1 kg/mol acid doping.

7. An apparatus comprising:
    a housing with first and second internal chambers divided by a separator and an aperture connecting the first chamber to atmosphere;
    a sensing electrode disposed within the first chamber;
    at least one additional electrode disposed within the second chamber;
    an acid doped ionic liquid electrolyte disposed within the second chamber, wherein the sensing and the at least one additional electrode further comprise platinum on carbon, wherein the acid doped ionic liquid electrolyte is acid doped with methanesulfonic acid, and wherein the sensing electrode and the at least one additional electrode are configured to provide an output in response to hydrogen sulfide entering through the aperture which is greater than an output in response to carbon monoxide.

8. The apparatus as in claim 7, wherein at least one of the sensing electrode or the at least one additional electrode comprises platinum black.

9. The apparatus as in claim 7, wherein at least one of the sensing electrode or the at least one additional electrode comprises substantially 5% platinum on carbon.

10. The apparatus as in claim 7, wherein the acid doped ionic liquid electrolyte comprises one of: 1-ethyl-3-methylimidazolium hydrogensulfate (EMIM.HS)+methanesulfonic acid (MSA), 1-ethyl-3-methylimidazolium methylsulfate (EMIM.MS)+MSA, 1,2,4-trimethylpyrazolium methylsulfate (TMP.MS)+MSA, N-n-butyl-N-methylpiperidinium bis (trifluoromethane)sulfonimide (BMPI.TFSI)+MSA, N,N,N',N'-tetraethylsulfamide TES.TFSI+MSA, N,N-dimethylethanolamine bis(trifluoromethane)sulfonimide (DMEA.TFSI)+MSA, or butyldiethanolamine bis(trifluoromethylsulfonyl)imide (BDEA.TFSI)+MSA.

11. The apparatus as in claim 7, wherein the acid doped ionic liquid electrolyte comprises about 1% acid doping.

12. The apparatus as in claim 7, wherein the acid doped ionic liquid electrolyte comprises about 0.1 kg/mol acid doping.

13. The apparatus as in claim 7, wherein the acid doped ionic liquid electrolyte comprises: 1-ethyl-3-methylimidazolium hydrogensulfate doped with 0.1 kg/mol methanesulfonic acid, N,N-Dimethylethanolammonium bis(trifluoromethylsulfonyl)amide doped with 0.1 kg/mol methanesulfonic acid, or 1,2,4-trimethylpyrazolium methylsulfate doped with 1% methanesulfonic acid.

14. An apparatus comprising:
    a housing with first and second internal chambers divided by a separator and an aperture connecting the first chamber to atmosphere;
    a sensing electrode disposed within the first chamber;
    at least one additional electrode disposed within the second chamber;
    an acid doped ionic liquid electrolyte disposed within the second chamber and saturating the separator thereby causing the sensing electrode to provide an output in response to hydrogen sulfide entering through the aperture, wherein the sensing and the at least one additional electrode further comprise platinum, wherein the acid doped ionic liquid electrolyte is acid doped with bis (trifluoromethane)sulfonimide acid, and wherein the sensing electrode is configured to provide an output in response to carbon monoxide that is less than an output in response to hydrogen sulfide.

15. The apparatus as in claim 14, wherein the acid doped ionic liquid electrolyte comprises about 1% acid doping.

16. The apparatus as in claim 14, wherein the acid doped ionic liquid electrolyte comprises about 0.1 kg/mol acid doping.

17. The apparatus as in claim 14, wherein the acid doped ionic liquid electrolyte comprises: 1-ethyl-3-methylimidazolium hydrogensulfate, N,N-Dimethylethanolammonium bis(trifluoromethylsulfonyl)amide, or 1,2,4-trimethylpyrazolium methylsulfate.

* * * * *

UNITED STATES PATENT AND TRADEMARK OFFICE
CERTIFICATE OF CORRECTION

Page 1 of 1

PATENT NO. : 9,835,581 B2
APPLICATION NO. : 14/037959
DATED : December 5, 2017
INVENTOR(S) : John Chapples and Martin Geoffrey Jones It is certified that error appears in the above-identified patent and that said Letters Patent is hereby corrected as shown below:

In the Specification

Column 4, Line 11: after "+" insert --MSA,--

Column 4, Line 14: "(BMPL.TFSI), BMPL." should be "(BMPI.TFSI), BMPI."

In the Claims

Column 6, Line 50: "bis" should be "bis(trifluoromethane)sulfonamide"

Signed and Sealed this
Twenty-fourth Day of April, 2018

Andrei Iancu
*Director of the United States Patent and Trademark Office*